United States Patent [19]
Trosken

[11] 3,966,826
[45] June 29, 1976

[54] PHENYL ETHERS

[75] Inventor: Jürgen Trösken, Walldorf, Germany

[73] Assignee: Hoechst Aktiengesellschaft, Frankfurt am Main, Germany

[22] Filed: July 8, 1975

[21] Appl. No.: 594,119

[30] Foreign Application Priority Data
July 10, 1974  Germany............................ 2433066

[52] U.S. Cl................................. 260/613 R; 71/122
[51] Int. Cl.².......................................... C07C 43/22
[58] Field of Search................................ 260/613 R

[56] References Cited
UNITED STATES PATENTS

| | | | |
|---|---|---|---|
| 3,420,892 | 1/1969 | Martin et al. | 260/612 R X |
| 3,506,720 | 4/1970 | Model et al. | 260/613 R |
| 3,798,276 | 3/1974 | Bayer et al. | 260/613 R X |
| 3,904,696 | 9/1975 | Model et al. | 260/613 R |

*Primary Examiner*—Bernard Helfin
*Attorney, Agent, or Firm*—Curtis, Morris & Safford

[57] ABSTRACT

Diphenyl ethers of the formula

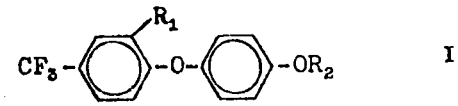

I wherein $R_1$ represents hydrogen or halogen and $R_2$ hydrogen or a monovalent cation, are intermediates for the manufacture of selective herbicides.

1 Claim, No Drawings

PHENYL ETHERS

The present invention provides novel diphenyl ethers of the formula

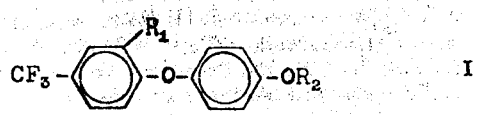

wherein $R_1$ represents hydrogen or halogen and $R_2$ hydrogen or a monovalent cation.

Compounds of formula I are obtained by reacting in known manner halogen compounds of the formula

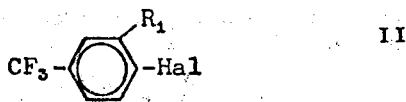

wherein Hal is halogen, with hydroquinone derivatives of the formula

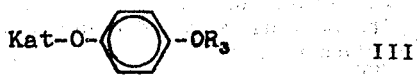

wherein Kat is a monovalent cation and $R_3$ may be $R^2$ or alkyl having from 1 to 4 carbon atoms, in a polar aprotic solvent at temperatures of from 120° to 200°C and by eliminating from the reaction product obtained an alkyl group in $R_3$-position by ether cleavage.

The process of the invention can be carried out in the presence or absence of copper or copper compounds as catalysts, but in case $R_1$ is hydrogen it is preferably carried out in the presence of catalytical quantities of copper or a copper compound. It is moreover preferable to operate as far as possible in the absence of water; water formed in the reaction, for example, in the preparation of alkali salts should therefore be removed, for example, by azeotropic distillation or by adding water binding substances. Alkyl radicals in $R_3$ position are split off in usual manner, for example with HBr in glacial acetic acid, with HJ, $AlCl_3$ or $AlBr_3$.

Preferred halogens in $R_1$ position are chlorine and bromine, especially chlorine. Hydrogen, alkali ions (Na,K ions) or ammonium ions are preferred substituents $R_2$. "Hal" also preferably represents chlorine and bromine, especially chlorine, and "Kat" stands preferably for alkali (Na,K) or ammonium.

Convenient solvents are those generally used for analogous reactions such as dimethyl sulfoxide, dimethyl formamide, dimethyl acetamide, diethyl acetamide, hexamethyl phosphoric acid trisamide, tetramethylene sulfone, tetramethyl urea, N-methyl pyrrolidone or nitrile such as aceto-nitrile.

The reactants of formulae I and II are preferably used in about stoichiometrical quantities, a slight excess of either component being possible.

If copper catalysts are used they are preferably present in amounts of 0.5 to 3 % by mole of copper per mole of the compound of formula II. Such copper compounds are those generally known for the Ullmann ether synthesis, for example $Cu_2O$ or elementary copper.

After termination of the reaction generally requiring 1 to 8 hours the reaction product is isolated in known manner, for example by filtering off the salt obtained and by distilling off the solvent or by pouring the mixture into water or on ice.

Surprisingly by an additional halogen in 3-position relative to the $CF_3$ group, even a atom, is not attacked although from U.S. Pat. specification No. 2,464,77 it is known that halogen in m-position to the $CF_3$ group may be exchanged for phenoxy in the reaction with phenolates.

The compounds of formula I are valuable intermediates for the manufacture of herbicides. For instance, when reacted with α-halopropionic acids or functional derivatives thereof they form the corresponding p-trifluoromethyl-phenoxy-phenoxypropionic acids and their derivatives, which have an excellent selective herbicidal action against monocotyledonous weeds (cf. Patent Application No. P 2 433,067.4) which corresponds to U.S. application Ser. No. 594,031 filed July 8, 1975.

The following examples illustrate the invention.

EXAMPLE 1

Potassium salt of 2-chloro-4-trifluoromethyl-4'-hydroxydiphenyl ether 112 g (2 moles) of KOH in 100 ml of water were added to 110 g of hydroquinone (1 mole) in 800 ml of dimethyl sulfoxide and 300 ml of toluene and refluxed at the water separator until all water was separated. Toluene was then distilled off until an inner temperature of about 170°C was obtained. 214.5 g (1 mole) of 3,4-dichlorobenzotrifluoride were then introduced dropwise at a temperature not exceeding 180°C. The hydroquinone salt then dissolved and potassium chloride precipitated, which was filtered off.

The solution of the potassium salt of 2-chloro-4-trifluoromethyl-4'-hydroxydiphenyl ether thus obtained could be further reacted directly for example, with α-bromo-propionic acid ethyl ester to give α-[4-(2'-chloro-4'-trifluoromethyl-phenoxy-)phenoxy]-propionic acid ethyl ester.

EXAMPLE 2

2-Chloro-4-trifluoromethyl-4'-hydroxy-diphenyl ether

The solution of potassium salt of 2-chloro-4-trifluoromethyl-4'-hydroxy-diphenyl ether obtained according to example (1) was poured on 2 liters of ice and acidified with 100 ml of concentrated HCl. The organic phase was separated, extracted with methylene chloride, dried over $Na_2SO_4$ and distilled. 208 g of 2-chloro-4-trifluoromethyl-4'-hydroxy-diphenyl ether were obtained of the formula

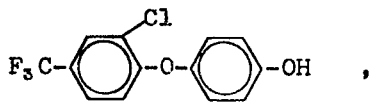

melting point 42° to 46°C (72 % of the theory calculated on hydroquinone).

EXAMPLE 3

2-Chloro-4-trifluoromethyl-4'-methoxy-diphenyl ether

An anhydrous phenolate solution was prepared by adding 40 g (1 mole) of NaOH in 50 ml of water to a solution of 124 g (1 mole) of hydroquinone-monomethyl ether in 300 ml of toluene and 500 ml of dimethyl sulfoxide and refluxing the mixture at the water separator.

Toluene was then distilled off in vacuo and 214,5 g (1 mole) of 3,4-dichlorobenzotrifluoride were added dropwise at 160°C. The reaction mixture was heated for 5 hours until it showed a neutral reaction. It was then poured on ice, the precipitate was filtered off with suction and recrystallized from aqueous methanol.

260 g of 2-chloro-4-trifluoromethyl-4'-methoxy-diphenyl ether were obtained of the formula

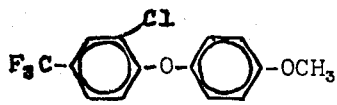

melting point 61° to 63°C, (86 % of the theory calculated on hydroquinone-monomethyl ether).

EXAMPLE 4

2-Chloro-4-trifluoromethyl-4'-hydroxy-diphenyl ether 66.7 g (0.22 mole) of 2-chloro-4-trifluoromethyl-4'-methoxy-diphenyl ether of example (3) were refluxed with 100 g of pyridine hydrochloride for 1.5 hours. The reaction product was poured on ice, the organic phase was separated and the aqueous layer was extracted with methylene chloride. The united organic phases were washed with diluted hydrochloric acid and the phenol formed was extracted with diluted sodium hydroxide solution. By acidifying the alkaline extract an oil was obtained which was separated. The acidified phases was extracted with methylene chloride, the united organic phases were dried and distilled. 53.2 g of 2-chloro-4-trifluoromethyl-4'-hydroxy-diphenyl ether were obtained of the formula

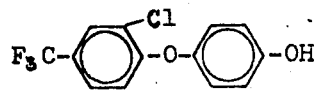

melting point 42° to 47°C (84 % of the theory calculated on the starting ether).

EXAMPLE 5

Preparation of 4-trifluoromethyl-4'-hydroxy-diphenyl ether

A solution of 110 g (1 mole) of hydroquinone in 800 ml of DMSO and 300 ml of toluene was refluxed at the water separator with 112 g of KOH in a small quantity of water to form the di-potassium salt. Toluene was distilled off until an inner temperature of 170°C was obtained and a small amount of copper bronze was added. Thereafter 180 g (1 mole) of p-chloro-benzotrifluoride were introduced dropwise at a temperature of about 170°C. The mixture obtained was stirred for 4 hours at 170°C, poured on 3 liters of ice and 100 ml of concentrated HCl and filtered off with suction. Distillation of the organic phase yielded 191 g of 4-trifluoromethyl-4'-hydroxydiphenyl ether of the formula

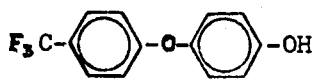

melting point 46° to 49°C, (76 % of the theory calculated on hydroquinone).

The following compounds of formula I were prepared in an analogous manner:

| Example No. | $R_1$ | $R_2$ | melting point |
|---|---|---|---|
| 6 | H | $CH_3$ | 37 to 38°C |
| 7 | Br | H | 89 to 93°C |
| 8 | Br | $CH_3$ | 64 to 68°C |

What is claimed is:
1. Diphenyl ethers of the formula

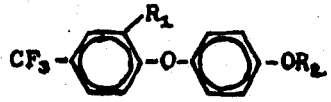

wherein $R_1$ is hydrogen or halogen and $R_2$ is hydrogen or an alkali metal or ammonium cation.

* * * * *